United States Patent [19]

Jacobs et al.

[11] Patent Number: 5,055,553
[45] Date of Patent: Oct. 8, 1991

[54] LOW MOLECULAR WEIGHT PULMONARY SURFACTANT PROTEINS

[75] Inventors: Kenneth A. Jacobs, Newton, Mass.; D. Randall Steinbrink, Phoenixville, Pa.; Joanna Floros; David S. Phelps, both of West Roxbury, Mass.; H. William Taeusch, Redondo Beach, Calif.

[73] Assignees: Genetics Institute Inc., Cambridge; The Brigham & Womens Hospital, Inc., Boston, both of Mass.

[21] Appl. No.: 507,331

[22] Filed: Apr. 9, 1990

Related U.S. Application Data

[60] Division of Ser. No. 190,287, May 4, 1988, Pat. No. 4,918,161, which is a continuation-in-part of Ser. No. 100,372, Sep. 24, 1987, Pat. No. 4,882,422, which is a continuation-in-part of Ser. No. 897,183, Aug. 15, 1986, abandoned, which is a continuation-in-part of Ser. No. 781,130, Sep. 26, 1985, abandoned.

[51] Int. Cl.$^5$ ............... A61K 37/02; C07H 19/00; C12P 19/28; C12N 5/00
[52] U.S. Cl. ............... 530/300; 530/324; 530/329; 536/22; 435/85; 435/240.1
[58] Field of Search ............... 530/300, 324, 329; 536/22; 435/85, 240.1

[56] References Cited

U.S. PATENT DOCUMENTS 4,659,805 4/1987 Schilling, Jr. et al. ............... 530/350
4,882,422 11/1989 Taeusch et al. ............... 530/350

OTHER PUBLICATIONS

Weinberg et al., "Isolation and Characterization of Human Apolipoprotein A-IV from Lipoprotein-Deleted Serum", J. Lipid Res., vol. 24, 1983, pp. 52-59.
Utermann et al., "Apolipoprotein A-IV: A Protein Occuring in Human Mesenteric Lymph Chylomicrons and Free in Plasma", Eur. J. Biochem. 99, 333-343 (1979).
Weisgraber et al., "Isolation and Characterization of an Apoprotein from the d>1.006 Lipoproteins of Human and Canine Lymph Homologous with the Rat A-IV Apoprotein", Biochem Biophys Res. Comm., vol. 85, No. 1, 1978, pp. 287-292.
Green et al., "Human Apolipoprotein A-IV-Intestinal Origin and Distriburion in Plasma", J. Clin. Invest., vol. 65, Apr. 1980, 911-919.
Beisiegel et al., "An Apolipoprotein Homolog of Rat Apolipoprotein A-IV in Human Plasma", Eur. J. Biochem. 93—601-608 (1979).
Floros et al., "Biosynthesis and in Vitro Translation of the Major Surfactant-Associated Protein from Human Lung", J. of Biol. Chem., vol. 260, No. 1, 495-500, Jan. 10, 1985.
Hawgood et al., "Effects of a Surfactant-Associated Protein and Calcium Ion on the Structure and Surface Activity of Lung Surfactant Lipids", Biochemistry, 1984, 24, 184-190.
Bhattacharyya et al., "Isolation and Characterization of Two-Hydroxyproline-Containing Glycoproteins from Normal Animal Lung Lavage and Lamellar Bodies", J. Clin. Invest., vol. 55, May 1975, 914-920.

Primary Examiner—Nathan M. Nutter
Attorney, Agent, or Firm—Bruce M. Eisen; David L. Berstein

[57] ABSTRACT

This invention relates to novel proteins useful for enhancing pulmonary surfactant activity, methods and materials for obtaining said proteins and compositions containing one or more of the proteins.

6 Claims, No Drawings

LOW MOLECULAR WEIGHT PULMONARY SURFACTANT PROTEINS

This application is a divisional application of U.S. Ser. No. 190,287 (filed May 4, 1988) and now U.S. Pat. No. 4,918,161, itself a continuation-in-part of U.S. Ser. Nos. 100,372 and now U.S. Pat. No. 4,882,422 (filed Sept. 24, 1987 as a CIP of 897,183 and 781,130); 897,183 (filed Aug. 15, 1986 as a CIP of 781,130) and now abandoned; and 781,130 (filed Sept. 26, 1985), and now abandoned, the contents of which are hereby incorporated by reference.

FIELD OF THE INVENTION

This invention relates to proteins originally isolated from human lung lavage, methods for obtaining said proteins and uses thereof.

BACKGROUND OF THE INVENTION

Throughout this application various publications are referenced. Full citations for these publications may be found at the end of the specification. The disclosure of these publications are hereby incorporated by reference in order to more fully describe the state of the art to which this invention pertains.

Hyaline Membrane Disease (HMD) and Respiratory Distress Syndrome (RDS) are synonymous terms denoting the clinical condition of pulmonary dysfunction in premature infants. The disease is attributable to the absence of surface active material (surfactant) which lines the air-alveolar interface in the lung and prevents collapse of the alveoli during respiration. Current therapy is predominantly supportive. However, recent clinical trials indicate that one promising therapy is the instillation of bovine-derived surfactant into the lungs of the neonate.

Surface tension in the alveoli of the lung is lowered by a lipoprotein complex called pulmonary surfactant. This complex consists of phospholipid and 5-10% protein (King, 1982). The protein fraction of the surfactant is composed of nonserum and serum proteins. The major surfactant associated protein is reportedly a 35,000 dalton nonserum, sialoglycoprotein (Shelly et al., 1982; Bhattacharyya et al, 1975; Sueishin and Benson 1981; King et al, 1973, Katyal & Singh, 1981). This protein reportedly seems to be important for the normal function of the pulmonary surfactant (King et. al., 1983; Hawgood et.al., 1985). It is present in reduced amounts in amniotic fluid samples taken shortly before the birth of infants who subsequently develop respiratory distress syndrome (Katyal and Singh, 1984; Shelly et al., 1982; King et al., 1975). Recently the biosynthesis of a 35,000 dalton protein in normal human lung tissue was studied and in an in vitro translation reaction, proteins of 29 and 31 kDa were identified as the primary translation products (Floros et al., 1985). A 35 kDa protein also accumulates in the lungs of patients with alveolar proteinosis (Battacharyya and Lynn, 1978, Battacharyya and Lynn, 1980a). This protein has the same electrophoretic mobility, immunological determinants and peptide mapping as the 35 kDa protein from normal human bronchoalveolar lavage material (Phelps et al., 1984; Whitsett et al., 1985).

In addition to the above mentioned proteins, the presence in rat lungs of a number of lower molecular weight surfactant-associated proteins has recently been reported. See D. L. Wang, A. Chandler and A. B. Fisher, Fed. Proc. 44(4): 1024 (1985), Abstract No. 3587 (ca. 9000 dalton rat protein) and S. Katyal and G. Singh, Fed. Proc. 44(6): 1890 (1985), Abstract No. 8639 (10,000-12,000 dalton rat protein).

Additionally, a Feb. 6, 1985 press release from California Biotechnology Inc. reports the cloning and "detailed manipulation" of "the gene encoding human lung surfactant protein." However, the press release does not characterize that protein or describe the "detailed manipulations." Two other reports of possible surfactant-related proteins have also been published recently, namely, J. A. Whitsett et al., 1986, Pediatr. Res. 20:460 and A. Takahashi et al., 1986, BBRC 135:527.

The present invention relates to a new group of proteins recovered and purified from lung lavage of patients with alveolar proteinosis; methods for obtaining the proteins; corresponding recombinant proteins; antibodies to the proteins (which may be obtained by conventional methods now that the proteins may be obtained in pure form) for use, e.g. in diagnostic products; compositions containing the novel proteins; and methods for using the compositions, e.g. in the treatment of infants afflicted with conditions such as Respiratory Distress Syndrome (RDS), as a drug delivery vehicle in the administration of other therapeutic materials to the lungs or other organs and in the treatment of adult RDS, which can occur during cardiopulmonary operations or in other situations when the lungs are filled with fluid and natural pulmonary surfactant production and/or function ceases.

SUMMARY OF THE INVENTION

This invention relates to novel purified forms of human proteins useful for enhancing pulmonary surfactant activity, methods for obtaining said proteins in purified form and compositions containing one or more of the proteins. The proteins of this invention include the following:

1. A purified protein, i.e. free or substantially free from other human proteins, characterized by:
   (a) solubility in 1-butanol at 4° C.;
   (b) substantial insolubility in 1-butanol at $-20°$ C., i.e. permitting protein precipitation therefrom;
   (c) containing the peptide sequence FPIPLPY-WL---AL (where "-" represents a non-determined amino acid residue); and,
   (d) a predominant band having an apparent molecular weight (MW) of $\sim 6$ kd as determined by SDS-PAGE analysis.

The protein so defined may be obtained and purified from lung lavage of patients suffering from alveolar proteinosis or may be produced by recombinant means, both as described herein, and should be useful in providing or enhancing enhancing pulmonary surfactant activity. Accordingly, this invention encompasses both the purified natural material as well as recombinant versions thereof. The amino acid composition of the protein as purified from lavage material is shown in Table 3. As described elsewhere herein, the recombinant form of the protein is encoded for by the DNA sequence of Table 1 or by a DNA sequence capable, or capable but for the use of synonymous codons, of hybridizing thereto under stringent conditions "Stringent conditions" as the phrase is used herein are hybridization conditions substantially equivalent to 65° C. in 5×SSC (1×SSC=150 mM NaCl/0.15M Na Citrate). Thus this invention also encompasses proteins which are at least about 90% homologous, and preferably at least about 95% homologous, to polypeptide sequences encoded by the DNA sequence of Table 1.

2. A purified protein, i.e. free or substantially free from other human proteins, characterized by:
(a) solubility in 1-butanol at −20° C.;
(b) a predominant band having an apparent MW of about 6 kd as determined by SDS-PAGE; and,
(c) an amino acid composition substantially as set forth in Table 2.

This protein should also be useful in providing or enhancing enhancing pulmonary surfactant activity.

TABLE 1

DNA and Corresponding Protein Sequence of 6K Clone

```
         10                  28                  43
GAATTCCGGT GCC ATG GCT GAG TCA CAC CTG CTG CAG TGG CTG CTG CTG CTG CTG
           MET Ala Glu Ser His Leu Leu Gln Trp Leu Leu Leu Leu Leu 58                  73                  88                  103
CCC ACG CTC TGT GGC CCA GGC ACT GCT GCC TGG ACC ACC TCA TCC TTG GCC TGT
Pro Thr Leu Cys Gly Pro Gly Thr Ala Ala Trp Thr Thr Ser Ser Leu Ala Cys 118                 133                 148                 163
GCC CAG GGC CCT GAG TTC TGG TGC CAA AGC CTG GAG CAA GCA TTG CAG TGC AGA
Ala Gln Gly Pro Glu Phe Trp Cys Gln Ser Leu Glu Gln Ala Leu Gln Cys Arg 178                 193                 208
GCC CTA GGG CAT TGC CTA CAG GAA GTC TGG GGA CAT GTG GGA GCC GAT GAC CTA
Ala Leu Gly His Cys Leu Gln Glu Val Trp Gly His Val Gly Ala Asp Asp Leu 223                 238                 253                 268
TGC CAA GAG TGT GAG GAC ATC GTC CAC ATC CTT AAC AAG ATG GCC AAG GAG GCC
Cys Gln Glu Cys Glu Asp Ile Val His Ile Leu Asn Lys MET Ala Lys Glu Ala 283                 298                 313
ATT TTC CAG GAC ACG ATG AGG AAG TTC CTG GAG CAG GAG TGC AAC GTC CTC CCC
Ile Phe Gln Asp Thr MET Arg Lys Phe Leu Glu Gln Glu Cys Asn Val Leu Pro 328                 343                 358                 373
TTG AAG CTG CTC ATG CCC CAG TGC AAC CAA GTG CTT GAC GAC TAC TTC CCC CTG
Leu Lys Leu Leu MET Pro Gln Cys Asn Gln Val Leu Asp Asp Tyr Phe Pro Leu 388                 403                 418                 433
GTC ATC GAC TAC TTC CAG AAC CAG ACT GAC TCA AAC GGC ATC TGT ATG CAC CTG
Val Ile Asp Tyr Phe Gln Asn Gln Thr Asp Ser Asn Gly Ile Cys MET His Leu 448                 463                 478
GGC CTG TGC AAA TCC CGG CAG CCA GAG CCA GAG CAG GAG CCA GGG ATG TCA GAC
Gly Leu Cys Lys Ser Arg Gln Pro Glu Pro Glu Gln Glu Pro Gly MET Ser Asp 493                 508                 523                 538
CCC CTG CCC AAA CCT CTG CGG GAC CCT CTG CCA GAC CCT CTG CTG GAC AAG CTC
Pro Leu Pro Lys Pro Leu Arg Asp Pro Leu Pro Asp Pro Leu Leu Asp Lys Leu 553                 568                 583
GTC CTC CCT GTG CTG CCC GGG GCC CTC CAG GCG AAG CCT GGG CCT CAC ACA CAG
Val Leu Pro Val Leu Pro Gly Ala Leu Gln Ala Arg Pro Gly Pro His Thr Gln 598                 613                 628                 643
GAT CTC TCC GAG CAG CAA TTC CCC ATT CCT CTC CCC TAT TGC TGG CTC TGC AGG
Asp Leu Ser Glu Gln Gln Phe Pro Ile Pro Leu Pro Tyr Cys Trp Leu Cys Arg 658                 673                 688                 703
GCT CTG ATC AAG CGG ATC CAA GCC ATG ATT CCC AAG GGT GCG CTA GCT GTG GCA
Ala Leu Ile Lys Arg Ile Gln Ala MET Ile Pro Lys Gly Ala Leu Ala Val Ala 718                 733                 748
GTG GCC CAG GTG TGC CGC GTG GTA CCT CTG GTG GCG GGC GGC ATC TGC CAG TGC
Val Ala Gln Val Cys Arg Val Val Pro Leu Val Ala Gly Gly Ile Cys Gln Cys 763                 778                 793                 808
CTG GCT GAG CGC TAC TCC GTC ATC CTG CTC GAC ACG CTG CTG GGC CGC ATG CTG
Leu Ala Glu Arg Tyr Ser Val Ile Leu Leu Asp Thr Leu Leu Gly Arg MET Leu 823                 838                 853
CCC CAG CTG GTC TGC CGC CTC GTC CTC CGG TGC TCC ATG GAT GAC AGC GCT GGC
Pro Gln Leu Val Cys Arg Leu Val Leu Arg Cys Ser MET Asp Asp Ser Ala Gly 868                 883                 898                 913
CCA AGG TCG CCG ACA GGA GAA TGG CTG CCG CGA GAC TCT GAG TGC CAC CTC TGC
Pro Arg Ser Pro Thr Gly Glu Trp Leu Pro Arg Asp Ser Glu Cys His Leu Cys 928                 943                 958                 973
ATG TCC GTG ACC ACC CAG GCC GGG AAC AGC AGC GAG CAG GCC ATA CCA CAG GCA
MET Ser Val Thr Thr Gln Ala Gly Asn Ser Ser Glu Gln Ala Ile Pro Gln Ala
```

TABLE 1-continued
DNA and Corresponding Protein Sequence of 6K Clone

```
           988                 1003                1018
ATG CTC CAG GCC TGT GTT GGC TCC TGG CTG GAC AGG GAA AAG TGC AAG CAA TTT
MET Leu Gln Ala Cys Val Gly Ser Trp Leu Asp Arg Glu Lys Cys Lys Gln Phe 1033                1048                1063                1078
GTG GAG CAG CAC ACG CCC CAG CTG CTG ACC CTG GTG CCC AGG GGC TGG GAT GCC
Val Glu Gln His Thr Pro Gln Leu Leu Thr Leu Val Pro Arg Gly Trp Asp Ala 1093                1108                1123
CAC ACC ACC TGC CAG GCC CTC GGG GTG TGT GGG ACC ATG TCC AGC CCT CTC CAG
His Thr Thr Cys Gln Ala Leu Gly Val Cys Gly Thr MET Ser Ser Pro Leu Gln 1138          1153           1166        1176        1186        1196
TGT ATC CAC AGC CCC GAC CTT TGATGAGAAC TCAGCTGTCC AGCTGCAAAG GAAAAGCCAA
Cys Ile His Ser Pro Asp Leu 1206       1216       1226       1236       1246       1256       1266
GTGAGACGGG CTCTGGGACC ATGGTGACCA GGCTCTTCCC CTGCTCCCTG GCCCTCGCCA GCTGCCAGGC 1276       1286       1296       1306       1316       1326       1336
TGAAAAGAAG CCTCAGCTCC CACACCGCCC TCCTCACCTC CCTTCCTCGG CAGTCACTTC CACTGGTGGA 1346       1356       1366       1376       1386       1396       1406
CCACGGGCCC CCAGCCCTGT GTCGGCCTTG TCTGTCTCAG CTCAACCACA GTCTGACACC AGAGCCCACT 1416       1426       1436       1446       1456       1466       1476
TCCATCCTCT CTGGTGTGAG GCACAGCGAG GGCAGCATCT GGAGGAGCTC TGCAGCCTCC ACACCTACCA 1486       1496       1506       1516       1526       1536       1546
CGACCTCCCA GGGCTGGGCT CAGGAAAAAC CAGCCACTGC TTTACAGGAC AGGGGGTTGA AGCTGAGCCC 1556       1566       1576       1586       1596       1606       1616
CGCCTCACAC CCACCCCCAT GCACTCAAAG ATTGGATTTT ACAGCTACTT GCAATTCAAA ATTCAGAAGA 1626       1636       1646       1656       1666       1676       1686
ATAAAAAATG GAACATACA GAACTCTAAA AGATAGACAT CAGAAATTGT TAAGTTAAGC TTTTTCAAAA 1696       1706       1716       1726       1736       1746       1756
AATCAGCAAT TCCCCAGCGT AGTCAAGGGT GGACACTGCA CGCTCTGGCA TGATGGGATG GCGACCGGGC 1766       1776       1786       1796       1806       1816       1826
AAGCTTTCTT CCTCGAGATG CTCTGCTGCT TGAGAGCTAT TGCTTTGTTA AGATATAAAA AGGGGTTTCT 1836       1846       1856       1866       1876       1886       1896
TTTTGTCTTT CTGTAAGGTG GACTTCCAGC TTTTGATTGA AAGTCCTAGG GTGATTCTAT TTCTGCTGTG 1906       1916       1926       1936       1946       1956       1966
ATTTATCTGC TGAAAGCTCA GCTGGGGTTG TGCAAGCTAG GGACCCATTC CTGTGTAATA CAATGTCTGC 1976       1986       1996       2006       2016       2026
ACCAATGCTA ATAAAGTCCT ATTCTCTTTT AAAAAAAAAA AAAAAAAAAA AACGGAATTC
```

Deduced protein sequence of 6Kd PSP protein is underlined

TABLES 2 & 3

| Amino acid compositions of the cold butanol insoluble and soluble "6 kd" proteins, respectively | | |
|---|---|---|
|  | TABLE 3 | TABLE 2 |
| Asp/Asn | 3.06 | 2.7 |
| Thr | 1.18 | 2.0 |
| Ser | 2.55 | 2.1 |
| Glu/Gln | 5.97 | 1.6 |
| Pro | 7.64 | 6.3 |
| Gly | 7.38 | 22.9 |
| Ala | 9.13 | 3.3 |
| Cys | 9.14 | 0.95 |
| Val | 10.13 | 5.5 |
| Met | 3.46 | 3.4 |
| Ile | 6.46 | 4.8 |
| Leu | 16.23 | 17.3 |
| Tyr | 2.31 | 3.3 |
| Phe | 1.55 | 6.3 |
| His | .34 | 2.9 |
| Lys | 1.62 | 3.6 |
| Arg | 7.88 | 1.94 |

(calculated based on MW = 10,000 daltons; ave residue MW = 110)

Both proteins are referred to herein as "6 kd" proteins for the sake of simplicity, although it should be appreciated that other minor bands believed to represent incompletely processed forms of the proteins (e.g. at ~12 kd and/or ~16–18 kd) are also observed upon SDS-PAGE analysis of the proteins.

DETAILED DESCRIPTION OF THE INVENTION

The proteins of this invention were obtained by subjecting pulmonary lavage material from an alveolar proteinosis patient to a combination of separation techniques followed by chromatographic purification. More specifically, the lavage material was centrifuged, and the protein-containing pellet so obtained was washed with buffer and extracted with a solvent such as 1-butanol to remove lipids and lipid-associated proteins. The butanol extract was set aside and treated as described below.

The 1-butanol-insoluble material was then washed, redissolved in buffer and purified chromatographically. Two proteins were thus obtained which are characterized by a molecular weight of about 35 kd. Those proteins are described in greater detail in in Published International Application WO 86/02037.

Butanol-soluble proteins were obtained by cryoprecipitation. More specifically, storage of the 1-butanol extract at −20° C. yielded a precipitate which was purified chromatographically to yield a protein characterized by a predominant band having an apparent molecular weight of about 6 kd (as determined by SDS-PAGE) and the observed amino acid composition set forth in Table 3. A second 6 kd (as determined by SDS-PAGE) protein was obtained by concentrating the supernatant to dryness and purifying the residue chromatographically. The observed amino acid composition of the latter 6 kd protein is set forth in Table 2.

The two low molecular weight proteins of this invention differ significantly from each other with respect to amino acid composition, as well as from the protein described by Tanaka, Chem. Pharm. Bull. 311:4100 (1983). Additionally, the N-terminal peptide sequence of the cold butanol-insoluble 6 kd protein was determined (Table 4). As previously mentioned, for the sake of simplicity, both low molecular weight PSP proteins are referred to hereinafter as "6k" proteins based on the approximate apparent molecular weights of their predominant protein bands as determined by conventional SDS-PAGE. It should be understood, however, that the actual molecular weights of these protein bands are presumably in the range of ~5-~9 kilodaltons.

The fact that these proteins can now be obtained in pure form by the above-described methods made it possible for one to apply conventional methods to elucidate the amino acid composition and sequence of the proteins; to prepare oligonucleotide probes based on the elucidated peptide sequences; to identify genomic DNA or cDNA encoding the proteins by conventional means, e.g., via (a) hybridization of labeled oligonucleotide probes to DNA of an appropriate library (Jacobs et al., 1985), (b) expression cloning (Wong et al., 1985) and screening for surfactant enhancing activity or (c) immunoreactivity of the expressed protein with antibodies to the proteins or fragments thereof; and to produce corresponding recombinant proteins using the identified genomic DNA or cDNA and conventional expression technology i.e. by culturing genetically engineered host cells such as microbial, insect or mammalian host cells containing the DNA so identified, for instance, transformed with the DNA or with an expression vector containing the DNA.

By way of example, genes encoding the two 35 kd proteins were cloned as described in detail in WO 86/02037.

Additionally, oligonucleotide probes based on the N-terminal sequence of the cold butanol-insoluble 6K protein (See Table 4) were synthesized and were used to screen a cDNA library prepared from human lung mRNA (Toole et al., 1984) as described in greater detail in Example 2, below. Several clones which hybridized to the probes were identified. Based on hybridization intensity one clone was selected, subcloned into M13 and sequenced. Plasmid PSP6K-17-3 was constructed by inserting the cloned cDNA so identified as an EcoRI fragment into the EcoRI site of plasmid SP65 (D. A. Melton et al., 1984, Nucleic Acids Res., 12:7035-7056). PSP6K-17-3 has been deposited with the ATCC under accession No. ATCC 40245. The nucleotide sequence of the cloned cDNA insert is shown in Table 1.

TABLE 4

| 1 | 5 | 10 |
|---|---|---|
| F P I P L P Y (—) W L (—) (—) A L | | |

(—) = Not determined (positions 8,11 & 12 were unidentified)

As those skilled in the art will appreciate, the cDNA insert in PSP6K-17-3 contains an open reading frame encoding a protein having a molecular weight of over 40kd. It is believed that the primary translation product is further processed, e.g., by Type II pneumocytes (Alveolar Type II cells), to yield the approximately 6K protein. It is contemplated that the cloned cDNA, portions thereof or sequences capable of hybridizing thereto under stringent conditions may be expressed in host cells or cell lines by conventional expression methods to produce "recombinant" proteins having surfactant or surfactant enhancing activity.

With respect to the cloned approximately 6K protein, this invention encompasses vectors containing a heterologous DNA sequence encoding the characteristic peptide sequence Ile through Cys corresponding to nucleotides A-656 through C-757 of the sequence shown in Table 1, i.e., IKRIQAMIPK-GALAVAVAQVCRVVPLVAGGICQC. One such vector contains the nucleotide sequence.

ATC AAG CGG ATC CAA GCC ATG ATT CCC AAG GGT
GCG CTA GCT GTG GCA GTG GCC CAG GTG TGC CGC
GTG GTA CCT CTG GTG GCG GGC GGC ATC TGC CAG
TGC

Other vectors of this invention contain a heterologous DNA sequence encoding at least a portion of the characteristic peptide sequence substantially as depicted in the underlined peptide region of Table 6, i.e., FPIPL-PYCWLCRALIKRIQAMIPK-GALAVAVAQVCRVVPLVAGGICQCLAERYS-VILLDTLLGRML. One such vector contains the DNA sequence substantially as depicted in the underlined nucleotide sequence of Table 1, i.e., TTC CCC ATT CCT CTC CCC TAT TGC TGG CTC TGC
AGG GCT CTG ATC AAG CGG ATC CAA GCC ATG ATT
CCC AAG GGT GCG CTA GCT GTG GCA GTG GCC CAG
GTG TGC CGC GTG GTA CCT CTG GTG GCG GGC GGC
ATC TGC CAG TGC CTG GCT GAG CGC TAC TCC GTC
ATC CTG CTC GAC ACG CTG CTG GGC ATG CTG Another exemplary vector contains a heterologous DNA sequence, such as the nucleotide sequence depicted in Table 1, which encodes the full-length peptide sequence of Table 1. DNA inserts for such vectors which comprise a DNA sequence shorter than the full-length cDNA of PSP6K-17-3, depicted in Table 1, may be synthesized by known methods, e.g. using an automated DNA synthesizer, or may be prepared from the full-length cDNA sequence by conventional methods such as loop-out mutagenesis or cleavage with restriction enzymes and ligation. Vectors so prepared may be used to express the subject proteins by conventional means or may be used in the assembly of vectors with larger cDNA inserts In the former case the vector will also contain a promoter to which the DNA insert is operatively linked and may additionally contain an amplifiable and/or selectable marker, all as is well known in the art.

The proteins of this invention may thus be produced by recovering and purifying the naturally-occuring proteins from human pulmonary lavage material as described herein. Alternatively, the corresponding "recombinant" proteins may be produced by expression of the DNA sequence encoding the desired protein by conventional expression methodology using microbial or insect or preferably, mammalian host cells. Suitable vectors as well as methods for inserting therein the desired DNA are well known in the art. Suitable host cells for transfection or transformation by such vectors and expression of the cDNA are also known in the art.

Mammalian cell expression vectors, for example, may be synthesized by techniques well known to those skilled in this art. The components of the vectors such as the bacterial replicons, selection genes, enhancers, promoters, and the like may be obtained from natural sources or synthesized by known procedures. See Kaufman, *Proc. Natl. Acad. Sci.* 82: 689–693 (1985).

Established cell lines, including transformed cell lines, are suitable as hosts. Normal diploid cells, cell strains derived from in vitro culture of primary tissue, as well as primary explants are also suitable. Candidate cells need not be genotypically deficient in the selection gene so long as the selection gene is dominantly acting.

The host cells preferably will be established mammalian cell lines. For stable integration of vector DNA into chromosomal DNA, and for subsequenct amplification of integrated vector DNA, both by conventional methods, CHO (Chinese hamster Ovary) cells are generally preferred. Alternatively, the vector DNA may include all or part of the bovine papilloma virus genome (Lusky et al., *Cell,* 36:391–401 (1984) and be carried in cell lines such as C127 mouse cells as a stable episomal element. Other usable mammalian cell lines include HeLa, COS-1 monkey cells, mouse L-929 cells, 3T3 lines derived from Swiss, Balb-c or NIH mice, BHK or HaK hamster cell lines and the like. Cell lines derived from Alveolar Type II cells may be preferred in certain cases such as expression of the 6K protein (alone or with one or more other proteins of this invention) using the cDNA insert from PSP6K-13-7 or a fragment thereof.

Stable transformants then are screened for expression of the product by standard immunological or enzymatic assays. The presence of the DNA encoding the proteins may be detected by standard procedures such as Southern blotting. Transient expression of the DNA encoding the proteins during the several days after introduction of the expression vector DNA into suitable host cells such as COS-1 monkey cells is measured without selection by activity or immunological assay of the proteins in the culture medium.

In the case of bacterial expression, the DNA encoding the protein may be further modified to contain preferred codons for bacterial expression as is known in the art and preferably is operatively linked in-frame to a nucleotide sequence encoding a secretory leader polypeptide permittng bacterial secretion of the mature variant protein, also as is known in the art. The compounds expressed in mammalian, insect or microbial host cells may then be recovered, purified, and/or characterized with respect to physicochemical, biochemical and/or clinical parameters, all by known methods.

One or more of the proteins of this invention may be combined with a pharmaceutically-acceptable fatty acid or lipid such as dipalmitoylphosphatidyl choline or with mixtures of such fatty acids or lipids which may be obtained from commercial sources or by conventional methods, or with natural surfactant lipids to provide a formulated pulmonary surfactant composition. Natural surfactant lipids may be extracted by known methods from lung lavage, e.g. bovine or human lung lavage. Typically the weight ratios of total lipids to total proteins in the composition will be about 20:1 to about 100:1. At the levels currently being tested in clinical trials, one dose of the surfactant composition corresponds to 1–2 mg of total protein and 98–99 mg of total lipid.

It is contemplated that certain subcombinations of one or more of the proteins of this invention with one or more of the proteins described in WO 86/02037 and compositions containing such subcombinations may be especially useful in the treatment of patients with particular clinical indications.

EXPERIMENTAL EXAMPLES

EXAMPLE 1

Isolation and Characterization of the Surfactant Associated Proteins

Pulmonary lavage (50 ml) from an alveolar proteinosis patient was centrifuged at 10,000×g for 5 min. The pellet was collected and washed 5 times in 20 mm Tris HCl, 0.5M NaCl, pH 7.4. The lipids and lipid-associated proteins were extracted from the washed pellet by shaking with 50 ml 1-butanol for 1 hr at room temperature.

The butanol extract so obtained was stored at −20° C. causing precipitation of one of the low MW proteins. The precipitate was collected by centrifugation and dried under vacuum. The butanol layer containing butanol-soluble protein was evaporated to dryness. The precipitated cold butanol insoluble protein and the cold butanol-soluble protein were then purified in parallel by the same method as follows. Each crude protein was separately dissolved in $CHCl_3$: MeOH (2:1, v/v), applied to Sephadex LH20 columns and eluted with $CHCl_3$:MeOH (2:1). The proteins were then analyzed by SDS-PAGE. Fractions containing the protein were pooled and evaporated to dryness. Amino acid composition was determined by hydrolysis in 6N HCl at 110° C. for 22 hrs followed by chromatography on a Beckman model 63000 amino acid analyzer. N-terminal sequence was determined on an Applied Biosystems 470A sequencer Molecular weights were determined on 10–20% gradient SDS polyacrylamide gels.

EXAMPLE 2

Screening of the cDNA Library and Sequencing of Clones for the 6Kd Proteins

Based on the first six amino acids of the sequence shown in Table 4 an oligonucleotide probe was synthesized. The probe consisted of six pools of 17 mers. Three of the pools each contained 128 different sequences, and three of the pools each contained 64 different sequences. Based on the first seven amino acids two pools of 20 mers were synthesized. These pools contained either 384 or 192 different sequences.

A cDNA library from human lung m was prepared as described in Toole et al., (1984) and screened with the total mixture of the six pools using tetramethylammoniumchloride as a hybridization solvent (Jacobs et al., 1985). Approximately 100,000 phage were screened, and 100 phage which hybridized to the probe were plaque purified. The phage were then pooled into groups of 25 and screened with the individual 17 mer and 20 mer pools. Six phage which hybridized most intensely to one of the 20 mer oligonucleotide probes and one of the corresponding 17 mer pools (pool 1447 containing 128 different sequences) were plaque purified. The 17 mer pool 1447 was divided into four pools of 32 different sequences and hybridized to a dot blot of DNA prepared from these phage.

Based on the hybridization intensity, DNA from one of these six phage were subcloned into M13 for DNA sequence analysis. A sequence corresponding in identity and position to the amino acids shown in Table 4 was obtained, confirming that the isolated clone coded for the approximately 6 kd cold butanol-insoluble protein found in the lavage material of alveolar proteinosis patients (see above).

The first clone obtained was presumed to be an incomplete copy of the mRNA because it lacked an initiating methionine, and was used to isolate longer clones. Two clones were completely sequenced by generating an ordered set of deletions with Bal 31 nuclease, recloning into other M13 vectors and sequencing via the dideoxynucleotide chain termination procedure (Viera and Messing, 1982; Sanger et al., 1977). One clone corresponded to a full-length copy of the type referred to as 17 (Table 1), the second began at nucleotide 148 of clone 17. Sequence of the 5' end of a third clone confirmed the sequence of the 5' end of clone 17. The clones are identical throughout the coding region and differ only at two positions in the 3' untranslated region.

As those of ordinary skill in this art will appreciate, the cloned gene may be conveniently obtained by excision from PSP6K-17-3 (ATCC No. 40245) or may be recloned using sequence information provided herein in Table 1.

REFERENCES

1. Bhattacharyya, S. N., and Lynn, W. S. (1978) Biochem. Biophys. Acta 537, 329–335
2. Bhattacharyya, S. N., and Lynn, W. S. (1980) Biochem. Biophys. Acta 625, 451–458
3. Bhattacharyya, S. N., Passero, M. A., DiAugustine, R. P., and Lynn, W. S. (1975) J. Clin. Invest. 55, 914–920
4. Floros, J., Phelps, D. S., and Taeusch, W. H. (1985) J. Biol. Chem. 260, 495–500
5. Hawgood, S., Benson, B. J., and Hamilton, Jr. R. L. (1985) Biochemistry 24, 184–190
6. Hunkapiller, M. W. and Hood, L. E. (1983) Methods in Enzymology 91, 486.
7. Jacobs, K., Shoemaker, C., Rudersdorf, R., Neil, S. D., Kaufman, R. J., Mufson, A., Seehra, J., Jones, S. S., Hewick, R., Fritsch, E. E., Kawakita, M., Shimizu, T., and Miyake, T. (1985) Nature (Lond.) 313, 806–810.
8. Kafatos, E., Jones, W. C., and Efstratiadis, A. (1979) Nucleic acid Rest. 7, 1541–1552.
9. Katyal, S. L., Amenta, J. S., Singh, G., and Silverman, J. A. (1984) Am. J. Obstet. Gynecol. 148, 48–53.
10. Katyal, S. L. and Singh, G. (1981) Biochem. Biophys. Acta 670, 323–331.
11. King, R. J., Carmichael, M. C., and Horowitz, P.M. (1983) J. Biol. Chem. 258, 10672–10680.
12. King, R. J. (1982) J. Appl. Physiol. Exercise Physiol. 53, 1–8.
13. King. R. J., Klass, D. J., Gikas, E. G., and Clements, J. A. (1973) Am. J. Physiol 224, 788–795.
14. King, R. J., Ruch, J., Gikas, E. G., Platzker, A. C. G., and Creasy, R. K. (1975) J. of Applied Phys. 39, 735–741.
15. Laemmli, U. K. (1970) Nature (Lond.) 227, 680–685.
16. Miller, J. S., Paterson, B. M., Ricciardi, R. P., Cohen, L and Roberts, B. E. (1983) Methods in Enzymology 101p. 650–674.
17. Phelps, D. S., Taeusch, W. H., Benson, B., and Hawgood, S. (1984) Biochem. Biophs. Acta, 791-226-238.
18. Shelley, S. A., Balis, J. U., Paciga, J. E., Knuppel, R. A., Ruffolo, E. H., and Bouis, P. J. (1982) Am. J. Obstet. Gynecol. 144, 224–228.
19. Sigrist, H., Sigrist-Nelson, K., and Gither, G. (1977) BBRC 74, 178, 184.
20. Sueishi, K., and Benson, G. J. (1981) Biochem. Biophys. Acta 665, 442–453.
21. Toole, J. J., Knopf, J. L., Wozney, J. M., Sultzman L. A., Bucker, J. L., Pittman, D. D., Kaufman, R. J., Brown, E., Shoemaker, C., Orr, E. C., Amphlett, G. W., Foster, W. G., Coe, M. L., Knutson, G. L., Eass, D. N., Hewick, R. M. (1984) Nature (Lond.) 312, 342–347.
22. Whitsett, J. A., Hull, W., Ross, G., and Weaver, T. (1985) Pediatric Res. 19, 501–508.
23. Wong, G. G. et al., 1985, Science, 228:810–815

What is claimed is:

1. A recombinant DNA sequence containing a heterologous nucleotide sequence encoding a pulmonary surfactant protein comprising the peptide sequence FPIPLPY.
2. A recombinant DNA sequence containing a heterologous nucleotide sequence encoding a pulmonary surfactant protein comprising the peptide sequence: IKRIQAMIPKGALAVAVAQVCRVVPLVAG-GICQC.
3. A recombinant DNA sequence containing a heterologous nucleotide sequence encoding a pulmonary surfactant protein comprising the peptide sequence FPIPLPYCWLCRALIKRIQAMIPK-GALAVAVAQVCRVVPLVAGGICQCLAERYS-VILLDTLLGRML.
4. A DNA comprising a nucleotide sequence selected from the group consisting of:
   (a) the cDNA insert in PSP6K-17-3 (ATCC 40245);
   (b) a fragment of the DNA sequence of (a); and,
   (c) a recombinant DNA sequence capable of hybridizing under stringent conditions to the cDNA insert of (a) or which would be so capable but for the use of synonymous codons.
5. A host cell containing and capable of expressing a DNA of any of claims 1–4.
6. A method for producing a pulmonary surfactant protein which comprises culturing a host cell of claim 5.

* * * * *